ated. A quantity of the ink is applied to a first roller the surface of which is engraved. The ink is evenly distributed over the roller using a doctor-blade set so as to wipe the roller surface clean and leave the ink only in the engravings. A second roller of resiliently deformable material is moved into contact with the inked roller so causing ink to be transferred to the surface of the second roller until equilibrium is reached and a sheet of the substrate to be inked or coated is introduced into the nip between the two rollers. Means is provided for cleaning the rollers after use. The second roller may be formed from two or more separate rollers spaced apart so as to define separate inking surfaces or may be in the form of a single roller having one or more annular grooves to define the different inking surfaces required.

United States Patent [19]
Kerchiss

[11] Patent Number: 4,522,057
[45] Date of Patent: Jun. 11, 1985

[54] PRINTING INK PROOFER
[75] Inventor: Roman R. Kerchiss, Royton, United Kingdom
[73] Assignee: RK Chemical Company Limited, England
[21] Appl. No.: 545,456
[22] Filed: Oct. 26, 1983
[51] Int. Cl.³ .............................................. G01N 33/32
[52] U.S. Cl. ...................................................... 73/150 R
[58] Field of Search ...................... 73/150, 863; 356/36
[56] References Cited
U.S. PATENT DOCUMENTS

| 1,939,814 | 12/1933 | Hoch  | 73/150 |
|-----------|---------|-------|--------|
| 2,243,674 | 5/1941  | Hoch  | 73/150 |
| 2,990,715 | 7/1961  | Bradt | 73/150 |

Primary Examiner—S. Clement Swisher
Attorney, Agent, or Firm—Nelson E. Kimmelman

[57] ABSTRACT
A method and apparatus for preparing a proof or sample of an ink (as herein defined) as a preliminary to its being employed in a printing or coating process to enable its color and coating capability to be determined.

20 Claims, 4 Drawing Figures

PRINTING INK PROOFER

DESCRIPTION

1. Field of Invention

This invention concerns a printing ink proofer and an improved method of proofing an ink or like materials.

2. Background to the Invention

The testing of inks inter alia for colour has previously entailed the application of controlled quantities of the ink onto a small scale printing machine and producing one or more sample prints or proofs to enable the covering qualities and colour of the ink to be ascertained.

The accuracy of such tests has relied on the accuracy in the measurement of the volume of ink applied to the machine, and this in turn tends to be directly attributable to the skill and care exercised by the operator.

One such device is described in our early U.S. Pat. No. 1,238,483.

It is an object of the present invention to provide an improved proofer for checking on the coating capability and colour of inks on paper and board and like materials.

DEFINITION

In the context of this application the expression 'ink' is intended to cover any liquid or fluid or paint or paste-like material employed in a coating or printing process.

SUMMARY OF THE INVENTION

According to one aspect of the present invention a method of preparing a proof or sample of an ink (as herein defined) as a preliminary to its being employed in a printing or coating process to enable its colour and coating capability to be determined comprises the steps of:

(1) applying a quantity of ink to a first roller formed of resiliently deformable material;

(2) bringing the first roller into contact with a second roller axially longer than the first, and engraved so as to form a large number of microscopic depressions therein into which the ink can become trapped;

(3) causing the ink to become evenly distributed over that part of the axial length of the second engraved roller which corresponds to the axial length of the first roller, using a so-called doctor blade set so as to wipe the engraved roller surface clean leaving the ink only in the depressions;

(4) controlling the pressure between the two rollers so as to first cause ink to be transferred from the depressions onto the surface of the second roller until equilibrium is reached;

(5) introducing into the nip betweeen the two rollers a sample of sheet material which is the same as or similar to that to which the ink is to be applied in a subsequent printing process and causing the ink on the surface of the first resiliently deformable roller to be applied as a coating to the said sheet material;

The resulting coating is found to be readily reproducible to a high level of accuracy by merely allowing the two rollers to continue to rotate together and re-establish a position of inking equilibrium before inserting another sample of sheet material therebetween.

If a reduced tone (or undertone) effect is required, a length of the sample sheet material is selected so as to be greater than the circumference of the transfer roller so that the sheet material will still be located in the nip after a complete revolution of the two rollers thereby preventing re-inking during the second revolution. During this latter, the ink available for coating the sheet material is that remaining in the depressions after the first pass of the sheet material.

Preferably the doctor blade is adjustable in both proximity and angle of inclination to the surface of the engraved roller. Typically the angle between the plane of the blade and the normal to the roller surface at the point of contact between the blade and the roller surface, is in the range 70°-85°.

Preferably force is applied to the hingeing frame to urge the first roller into contact with the second roller with the desired pressure therebetween.

The force may be obtained from one or more air cylinders.

In order to simulate different printing techniques, a number of differently engraved rollers may be provided and the appropriate one is selected according to the technique which is to be simulated.

Although reference has so far only been made to a single first roller, it is to be understood that the method is applicable to apparatus in which there is more than one first roller and in which the inking surfaces of the two or more first rollers are separate one from the other by virtue of grooves provided in the surface of the rollers if not actual axially spacing of the rollers along a shaft. The invention thus allows two or more different colours of ink or different types of ink or different shades of ink to be applied to different ones of the first rollers and for two proofing coatings to be laid down on the sheet material during a single pass between the rollers. This is of particular advantage where a direct comparison under the same conditions is required between one ink and another.

The method also allows for comparison of an unknown ink with known inks.

The method is particularly applicable to thick paste-like inks and relies for its success on the fact that the doctor blade can be set to clean the engraved roller just before the latter is due to engage the resilient roller and form the nip therebetween and a sheet of paper or similar sheet material introduced into the nip will therefore only have ink applied to that surface of the sheet material facing the resilient roller.

The pressure between the rollers is adjusted so that this desirable result is in practice normally obtained.

According to another aspect of the invention, apparatus for performing the method of the invention comprises:

(1) a first engraved roller having a plurality of microscopic depressions in its surface;

(2) a doctor blade adjustably mounted relative to the first roller, for co-operating with the roller to remove surplus ink from the surface of the roller and leave ink only in the depressions;

(3) at least two second rollers each of resiliently deformable material and axially separate at least at their inking surfaces, mounted for rotation about an axis parallel to the axis of rotation of the first, engraved, roller, and movable under pressure into contact with the engraved roller, and away therefrom, as required;

(4) means for adjusting the pressure exerted between the rollers;

(5) drive means for rotating at least the engraved roller at a controlled speed, and (6) sheet collecting means on the discharge side of the nip between the rollers for receiving and supporting a sheet of paper or like material after the latter has passed between the rollers and had ink applied thereto from the rollers.

By providing two separate rollers or at least a single roller having two separate inking surfaces separated by an annular groove, with the total extent of the resiliently deformable roller being less than that of the engraved roller, so different inks can be laid down as coatings on a single sheet of paper or like sheet material passed between the inked rollers and the engraved roller with the coating, as provided by the method of the invention, being laid down from the ink contained on the surface of the resiliently deformable rollers. In this way, direct comparison can be made between one ink and another.

It is to be understood that any number of separate inking surfaces may be provided by an appropriate number of subdivisions of the cylindrical surface of a single resiliently deformable roller or by means of a corresponding number of separate rollers mounted on a single shaft.

Preferably sheet feeding and guide means is located at the input to the nip.

Preferably means is provided for controlling the speed of rotation of the engraved roller.

Preferably means for indicating the speed of rotation of the engraved roller, is provided. Typically a tachometer is employed or alternatively a shaft encoder and electronic pulse counter and display are provided.

Preferably means is provided for adjusting the pressure exerted between the two rollers and for indicating said pressure.

Preferably means is provided for cleaning the rollers after use, typically in the form of a solvent both with or without solvent applicator roller and transfer rollers.

Preferably means is provided for adjusting both the angle and spacing of the doctor blade relative to the engraved roller.

The engraving of the first roller is typically such as to provide between 100 and 400, typically 300, cavities per inch in both axial and circumferential directions of measurement around the first roller, ie typically 90,000 cavities per square inch of surface.

Typically the cavities are 6/10 of a thousandth of an inch, ie approximately 14 microns, deep, but deeper or shallower cavities may be employed in the range 0.2 to 2.00 thousandths of an inch.

Typically the engraved roller is a so-called Anilox roller.

Conveniently each second roller is of natural or synthetic rubber material or a plastics material such as polyurethane or a composite of rubber and plastics material.

Preferably the second rollers are mounted in a hingeing frame and are movable from an elevated position clear of the engraved roller, into a lower position in contact with the engraved roller.

Since printing ink and the like are often highly inflammable, the drive means for rotating the engraved roller is conveniently an air motor, and speed control is achieved by controlling the volume of air available to the air motor.

Typically the doctor blade is formed from a blade some two thousandths of an inch thick and a thicker rigid backing plate, and the two are sandwiched in a chuck, itself mounted for movement relative to the engraved roller.

Preferably both the resilient rollers and the engraved roller are mounted on shafts which are adapted to be readily inserted into and removed from, bearing assemblies and driving means is provided at least at one end for engaging one of the shafts and rotating same, so that different rollers can be substituted at will.

Typically an air motor is provided for driving the engraved roller shaft through reduction gearing so that the final speed of rotation of the shaft is of the order of 100 revolutions per minute. In a typical installation the motor will rotate at a speed of around 3000 rpm under no-load, reducing to approximately 1500 rpm under load and the reduction gearing (or gearbox) has a ratio of 18:1.

The method of applying the ink to the rollers (typically the resiliently deformable rollers) prior to the establishment of equilibrium and the passage of a sheet material between the rollers, is most conveniently attained using a spatula or the like and simply positioning a suitably sized blob of ink on to the surface of the roller to which the ink is to be applied. Running the rollers together and using the doctor blade will cause the ink to spread out and form an even film over the surface of the resiliently deformable roller to which the ink has been applied after equilibrium has been established.

Alternatively and in some ways more preferably, ink applicatior means may be provided for applying ink from a suitable reservoir or container to the cylindrical surface of the roller to which the ink is to be applied. The ink applicator may in fact form part of or be associated with a cleaning device for cleaning the roller and removing therefrom all traces of the ink film applied thereto and to this end the ink applicator may be on one side and the ink remover on the other side of a rocking member which can be tilted so that either one or the other engages the roller.

The invention will now be described by way of example with reference to the accompanying drawings.

DETAILED DESCRIPTION OF THE DRAWINGS

Figure 1:
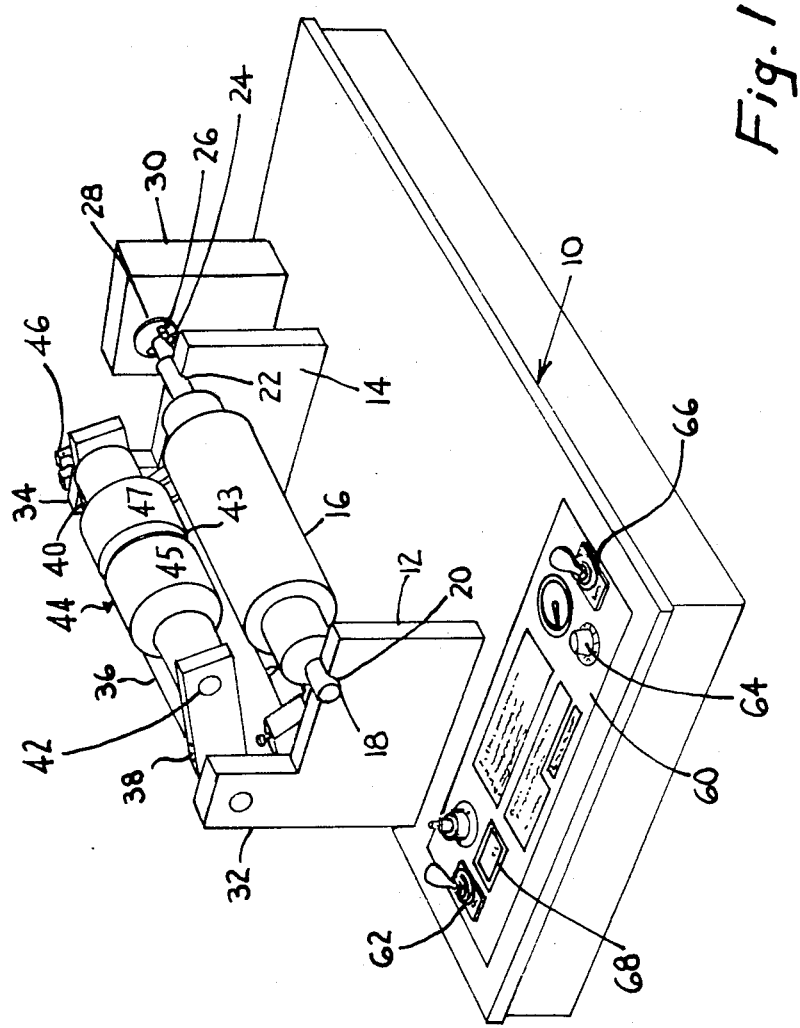
FIG. 1 is a perspective view of one embodiment of the invention.

A printing tester or proofer press is shown in the drawings as comprising a baseplate 10 carrying supports 12 and 14 for an engraved roller 16 carried by a shaft 18 which is rotatably received in half bearings at 20 and 22 and includes a drive take-up pin 24 which is engaged by a driving pin 26 extending off centre from a rotating plate 28 comprising the output of a gearbox 30.

The supports 12 and 14 include two elevated sections 32 and 34 within which are held captive the ends of a support shaft 36 on which are rigidly mounted two radius arms 38 and 40 which carry between their ends a shaft 42 on which is rotatable a rubber roller 44 serving as a transfer roller for co-operating with the engraved roller 16. The roller 44 includes a circular central annular groove 43 to define two inking surfaces 45 and 47.

Figure 2:
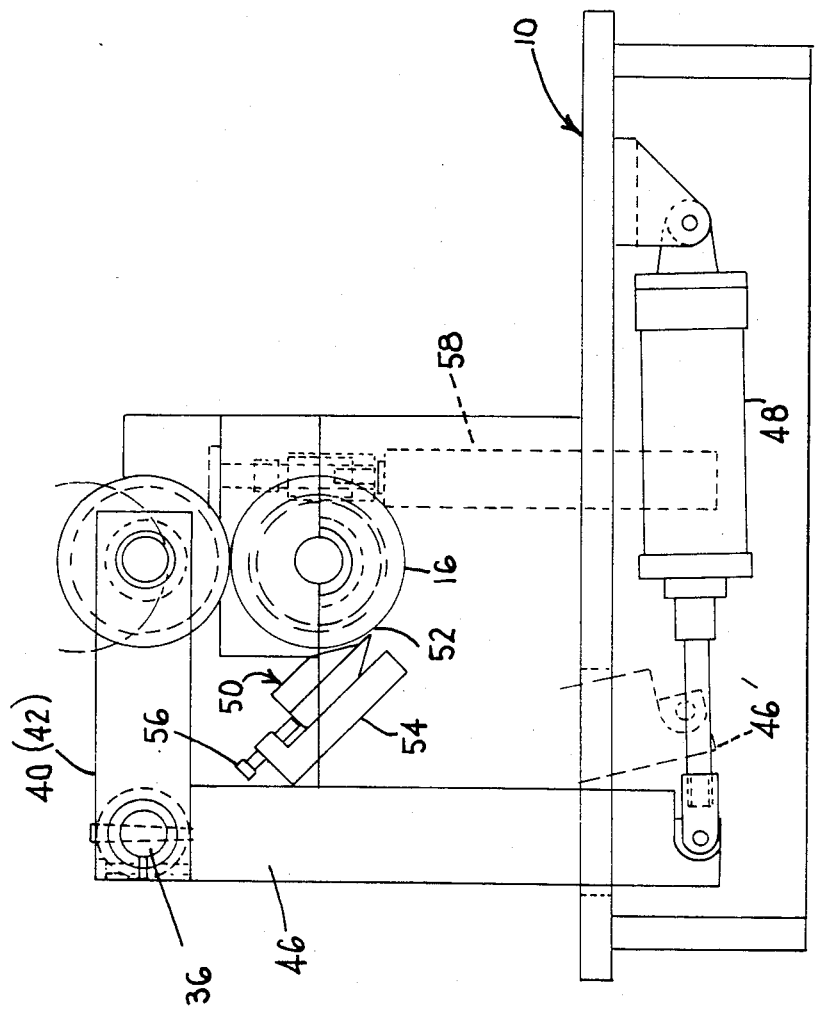
FIG. 2 is a side elevation of the apparatus shown in FIG. 1.

The roller 44 is movable into engagement with the roller 16 by rotation of the shaft 36 and to this end an arm 46 is rigidly attached to one end of the shaft 36 and as shown in FIG. 2, is acted on at its lower end by a pneumatic ram 48 the piston of which is movable outwardly to rotate shaft 36 clockwise as shown in FIG. 2. The retracted position is shown at 46'.

A doctor blade, best seen in FIG. 2, comprising a chuck 50 and blade 52, is movable relative to a support 54 by screw adjusters 56. Angle as well as spacing from the cylinder 16 is adjustable.

An air motor 58 is mounted within the gearbox housing 30 as shown in FIG. 2, and gears (not shown in detail) transmit drive therefrom to the shaft 18 as described.

Figure 4:
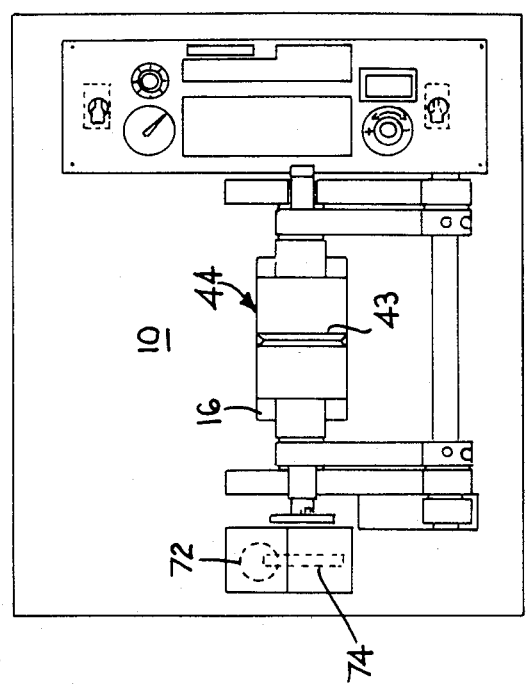
FIG. 4 is a plan view thereof.

As best seen in FIGS. 1 and 4, a control panel 60 is provided with an ON-OFF switch 62, motor speed control 64, UP-DOWN switch 66 and speed of rotation indicator 68.

Although not shown in detail the speed indicator 68 is an LED display device for displaying digits indicating the rotational speed in RPM and an electronic revolution counting device is provided with a shaft encoder (not shown) on the shaft 18.

Figure 3:
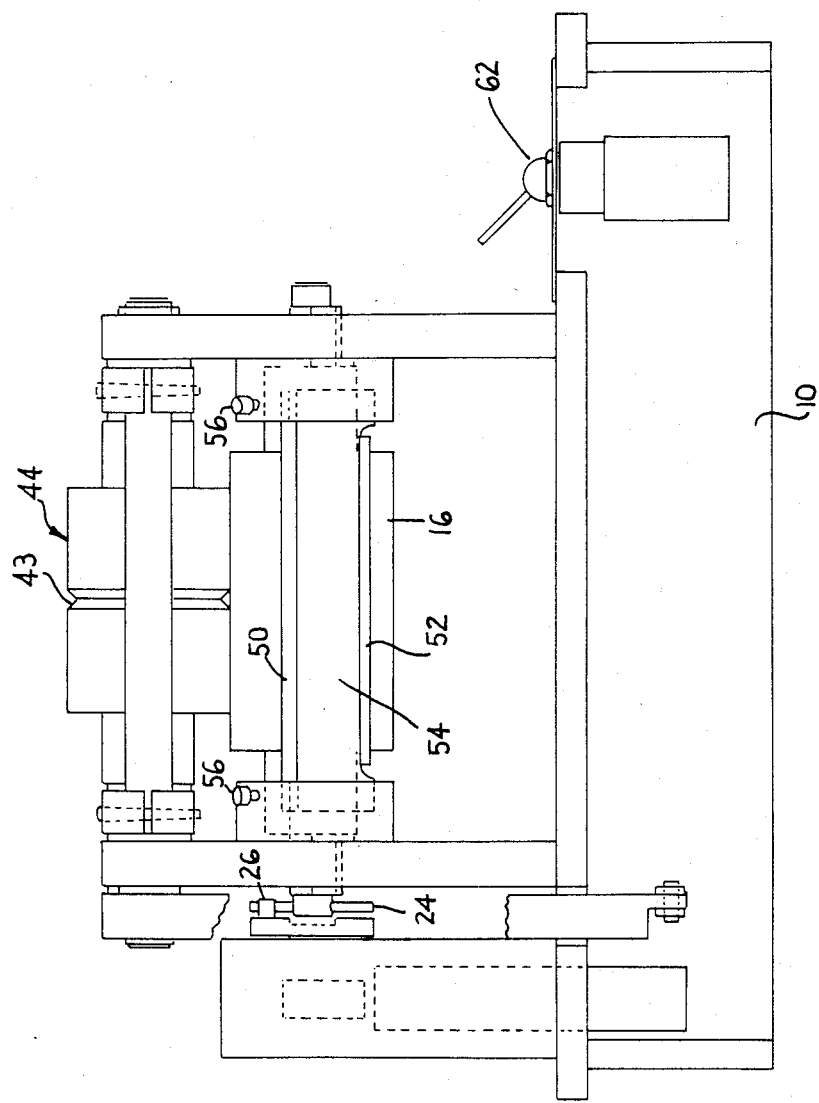
FIG. 3 is a front view of the apparatus of FIG. 1.

FIG. 3 shows the nip between the two rollers 16 and 44 between which a sheet of paper or the like is to be introduced, to obtain the proofing inking.

FIG. 4 shows inter alia meshing gears 72, 74 in the gearbox and illustrates the roller 44 in its lowered position particularly overlying the roller 16.

In use ink is applied to the inking surface 45 and/or 47 of the inking roller 44 and the latter is lowered on to the engraved roller 16. Mutual inking occurs with effective removal of the surplus ink from the surface of the roller 16 by means of the doctor blade and eventually equilibrium is reached in which a film of ink exists around the surfaces 45 and 47 of the roller 44 and the surface of the roller 16 is effectively free of ink, the latter being trapped in the cavities in the surface of the roller 16 formed by the engraving of the roller.

At this stage a sheet of paper or like sheet material can be introduced into the nip between the rollers 44 and 16 and a coating of ink will be applied from the inking surfaces 45 and 47 (if both have been inked) on to the surface of the sheet material which cooperates with the inking surfaces whilst little or no ink is applied to the underside of the paper from the engraved roller because of the action of the doctor blade.

The process is thus an exact opposite of a standard printing process in which ink is applied to an engraved roller for application from the engraved roller to a sheet of paper pressed into contact therewith in a nip formed between the ink engraved roller and non-inked resilient rollers. As is well known, in printing machines, any roller running with the inked engraved roller is not normally brought into contact with the latter, but only into contact with the back of a sheet of paper or like sheet material which itself is run in contact with the engraved inked roller and acts as a barrier between the inked surface of the engraved roller and the pressure rollers. In the event that ink is accidentally applied to pressure rollers in an ordinary printing machine, the machine has to be stopped and the accidentally inked pressure rollers cleaned before printing can recommence.

I claim:

1. A method of preparing a proof or sample of an ink (as herein defined) to enable its colour and coating capability to be determined as a preliminary to the ink being employed in a printing or coating process, comprising the steps of:
   (1) applying a quantity of ink to a resiliently deformable first roller;
   (2) bringing the first roller into rolling contact with a second roller which is engraved with microscopic ink-trapping depressions;
   (3) causing the ink on the first roller to be applied to the engraved second roller, using a doctor blade set to wipe clean the engraved roller surface and leave the ink only in depressions;
   (4) controlling the pressure between the first and second rollers so that ink is transferred from the depressions onto the surface of the first roller until equilibrium is reached;
   (5) introducing into the nip between the first and second rollers a sample of sheet material is equivalent to that to which the ink is to be applied in a subsequent printing process and causing the ink on the surface of the resiliently deformable first roller to be applied as a coating to the said sheet material.

2. A method as claimed in claim 1, in which the doctor blade is adjusted so that the angle between the plane of the blade and the normal to the roller surfaces at the point of contact between the blade and the roller surface, is in the range 70°–80°.

3. A method as claimed in claim 1, in which a force is applied to a hinged frame to urge the first roller into contact with the second roller with a predetermined pressure therebetween.

4. A method as claimed in claim 3, in which the force is obtained from at least one air cylinder.

5. A method as claimed in claim 1, in which the engraved roller is selected from a number of differently engraved rollers so as to enable different printing techniques to be simulated.

6. Ink proofing apparatus comprising:
   (1) a resiliently deformable first roller;
   (2) means for applying the ink to be tested to said first roller;
   (3) a second roller engraved with microscopic ink-trapping depressions;
   (4) means for rotationally driving at least one roller;
   (5) means for bringing the rollers into ink-transferring rolling contact;
   (6) a doctor blade arranged to wipe the surface of the second roller;
   (7) means for adjustng the contact pressure between the rollers in order to establish and maintain an equilibrium condition in which an ink coating is sustained on the first roller by ink trapped in the depressions of the second roller; and
   (8) a means for introducing into the nip between the rollers a sheet to be coated with ink from the surface of the first roller.

7. Apparatus according to claim 6, wherein the second roller is axially longer than the first roller.

8. Ink proofing apparatus comprising:
   (1) an engraved roller having a plurality of microscopic depressions in its surface;
   (2) a doctor blade adjustably mounted relative to said engraved roller, for co-operating with the roller to remove surplus ink from the surface thereof and leave ink only in the depressions;
   (3) roller means of resiliently deformable material and having axially separate inking surfaces, together with means mounting said roller means for rotation about an axis parallel to the axis of rotation of the engraved roller and means for moving the roller means into or out of rolling pressure contact with the engraved roller;

(4) means for adjusting the pressure of the rolling pressure contact between the engraved roller and the roller means; and (5) drive means for rotating at least the engraved roller at a controlled speed.

9. Apparatus according to claim 8, including sheet collecting means on the discharge side of the nip between the engraved roller and the roller means for receiving and supporting a sheet of paper material after the latter has passed between the roller and roller means and had ink applied thereto from the roller means.

10. Apparatus as claimed in claim 8, including sheet feeding and guide means located at the input to the nip between the engraved roller and the roller means.

11. Apparatus as claimed in claim 8, including means provided for controlling the speed of rotation of the engraved roller.

12. Apparatus as claimed in claim 8, including means for indicating the speed of rotation of the engraved roller.

13. Apparatus as claimed in claim 8, including means for indicating said pressure of the rolling pressure contact.

14. Apparatus as claimed in claim 8, including means for adjusting both the angle and spacing of the doctor blade relative to the enlarged roller.

15. Apparatus as claimed in claim 8, in which the engraving of the engraved roller is such as to provide between 100 to 400, typically 300, cavities per inch in both axial and circumferential directions of measurement around the engraved roller, and the cavities are in the range 0.2 to 2.00 thousandths of an inch deep.

16. Apparatus as claimed in claim 8, which the roller means is of a material selected from natural or synthetic rubber material, a plastics material such as polyurethane, and a composite of rubber and plastics material.

17. Apparatus as claimed in claim 8, in which the roller means is mounted in a hinged frame and is movable between an elevated position clear of the engraved roller and a lower position in contact with the engraved roller.

18. Apparatus as claimed in claim 8, in which the doctor blade is formed from a blade some two thoousandths of an inch thick and a thicker rigid backing plate, and the blade and backing are sandwiched in a chuck, itself mounted for movement relative to the engraved roller.

19. Apparatus as claimed in claim 8, in which both the engraved roller and the said resiliently deformable roller means are mounted on shafts which are replaceably mountable in bearing assemblies, the drive means engaging at least one of the shafts for rotating same through reduction gearing so that the final speed of rotation of the shaft is of the order of 100 revolutions per minute.

20. Apparatus as claimed in claim 8, in which the resiliently deformable roller means comprises a roller with at least one circumferential groove defining at least two cylindrical inking surfaces.

* * * * *